US006060064A

United States Patent [19]

Adams et al.

[11] Patent Number: 6,060,064

[45] Date of Patent: May 9, 2000

[54] CHIMERIC VIRUS-LIKE PARTICLE ANTIGEN PRESENTATION AND DELIVERY SYSTEM

[75] Inventors: Sally Elizabeth Adams, Oxford; Nigel Robert Burns, Abingdon; Simon Mark Richardson, Oxford, all of United Kingdom

[73] Assignee: British Biotech Pharmaceuticals Limited, Oxford, United Kingdom

[21] Appl. No.: 08/492,076

[22] PCT Filed: Dec. 24, 1993

[86] PCT No.: PCT/GB93/02656

§ 371 Date: Jun. 28, 1995

§ 102(e) Date: Jun. 28, 1995

[87] PCT Pub. No.: WO94/14969

PCT Pub. Date: Jul. 7, 1994

[30] Foreign Application Priority Data

Dec. 29, 1992 [GB] United Kingdom .................. 9227068

[51] Int. Cl.[7] .................................................. A61K 39/12

[52] U.S. Cl. ...................................... 424/199.1; 435/69.1

[58] Field of Search ............................ 435/172.3, 235.1, 435/236, 320.1; 424/199.1, 207.1

[56] References Cited

PUBLICATIONS

Adams et al., 1987 Nature 329:68–70.

Griffiths et al., 1991 J. Virol. 65:450–456.

Harris et al., 1992 Immunol. 77:315–321.

Reeck et al., 1987 Cell 50:667.

Lewin, 1987 Science 237:1570.

*Primary Examiner*—Laurie Scheiner
*Assistant Examiner*—Jeffrey S. Parkin
*Attorney, Agent, or Firm*—Banner & Witcoff, Ltd.

[57] ABSTRACT

Chimeric virus-like particles produced by a non-natural particle-forming protein. The non-natural particle forming protein comprises a self-assembling particle-forming first amino acid sequence substantially homologous with a yeast retrotransposon Ty p1 protein and a second amino acid sequence. The second sequence is antigenic and is incorporated within an epitope of the first amino acid sequence, which epitope, on particles formed from the first amino-acid sequence alone, is surface exposed. Particles formed from such proteins are immunogenic and can be used in immunotherapeutic or prophylactic vaccines or as diagnostic agents.

25 Claims, 8 Drawing Sheets

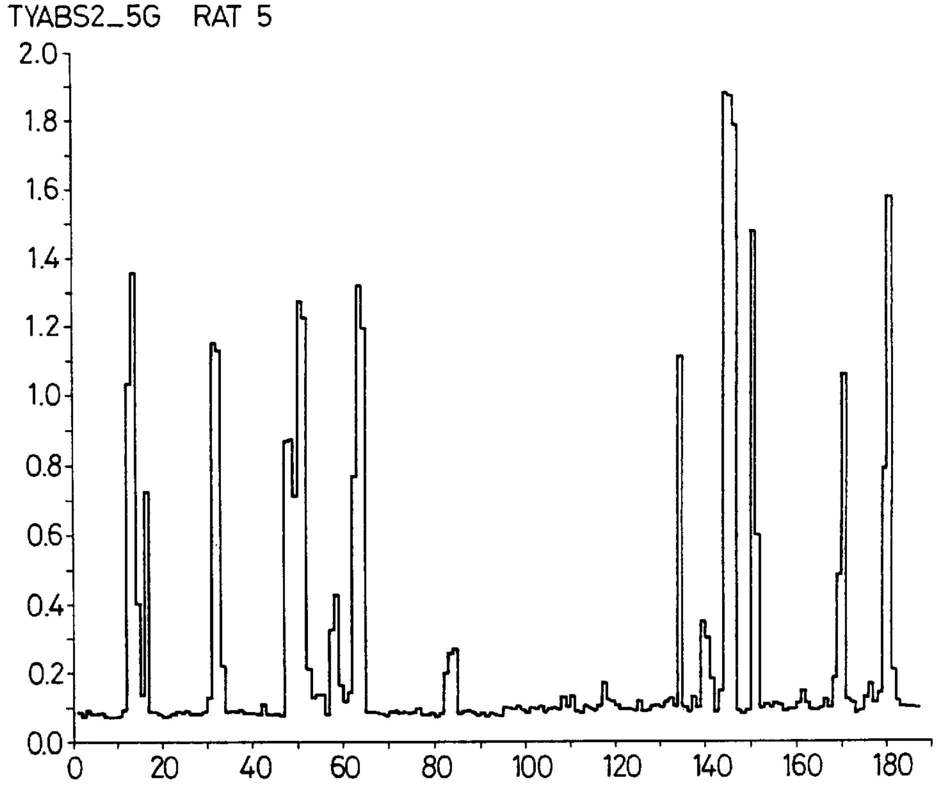
Fig.2a(I)
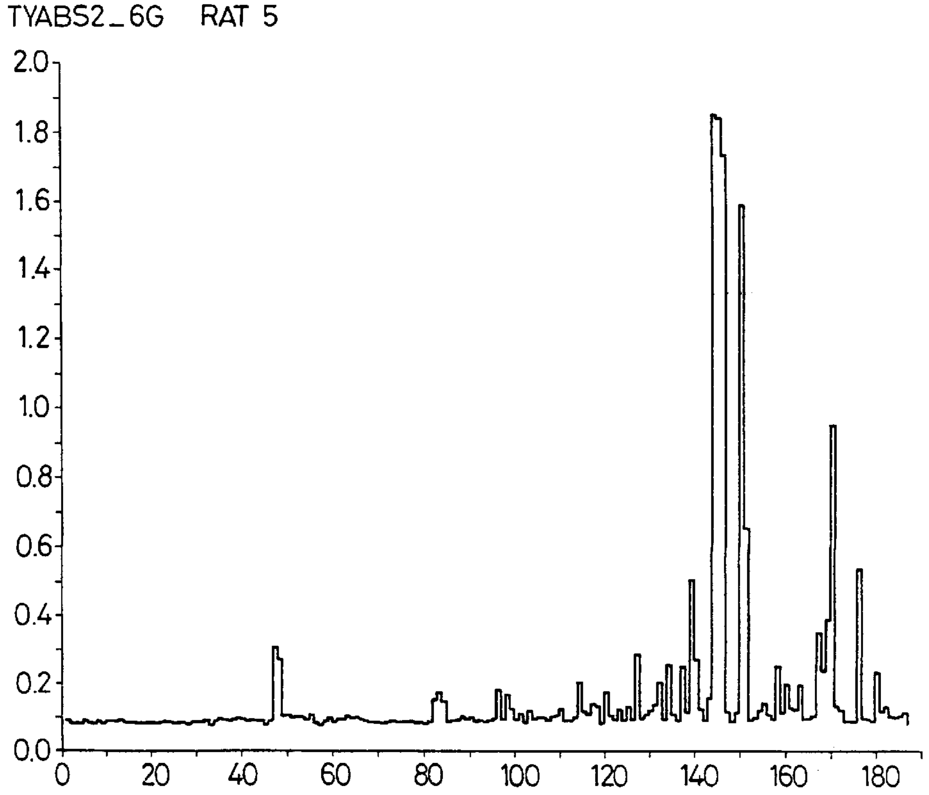
Fig.2a(II)

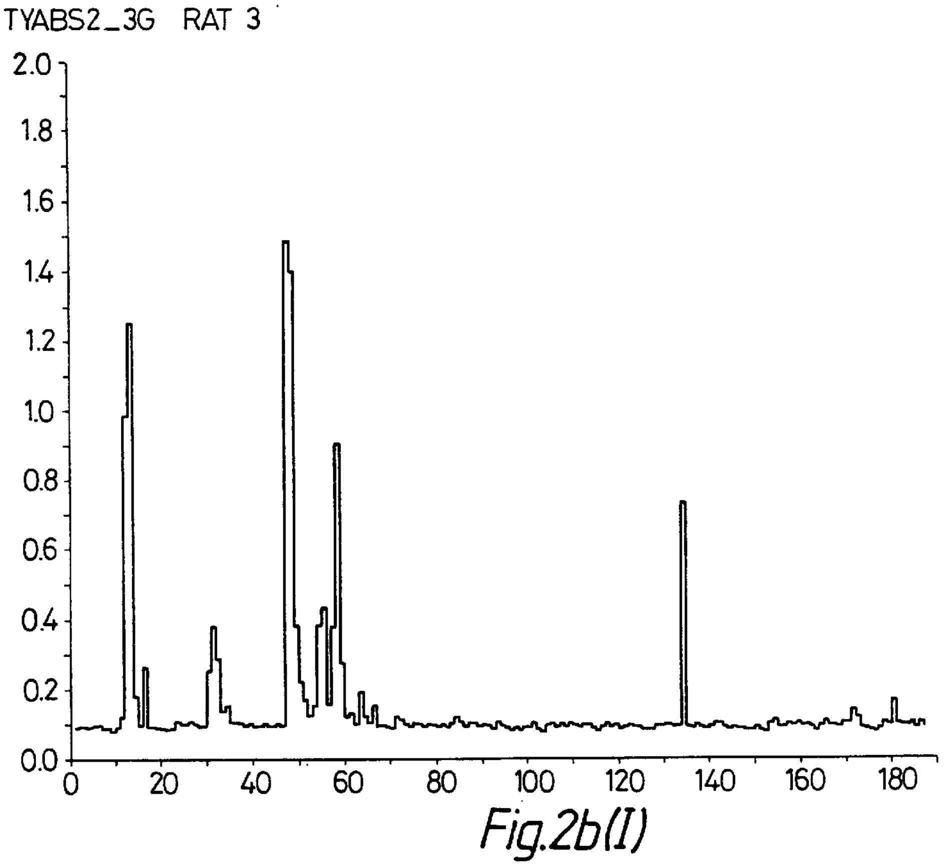
Fig.2b(I)
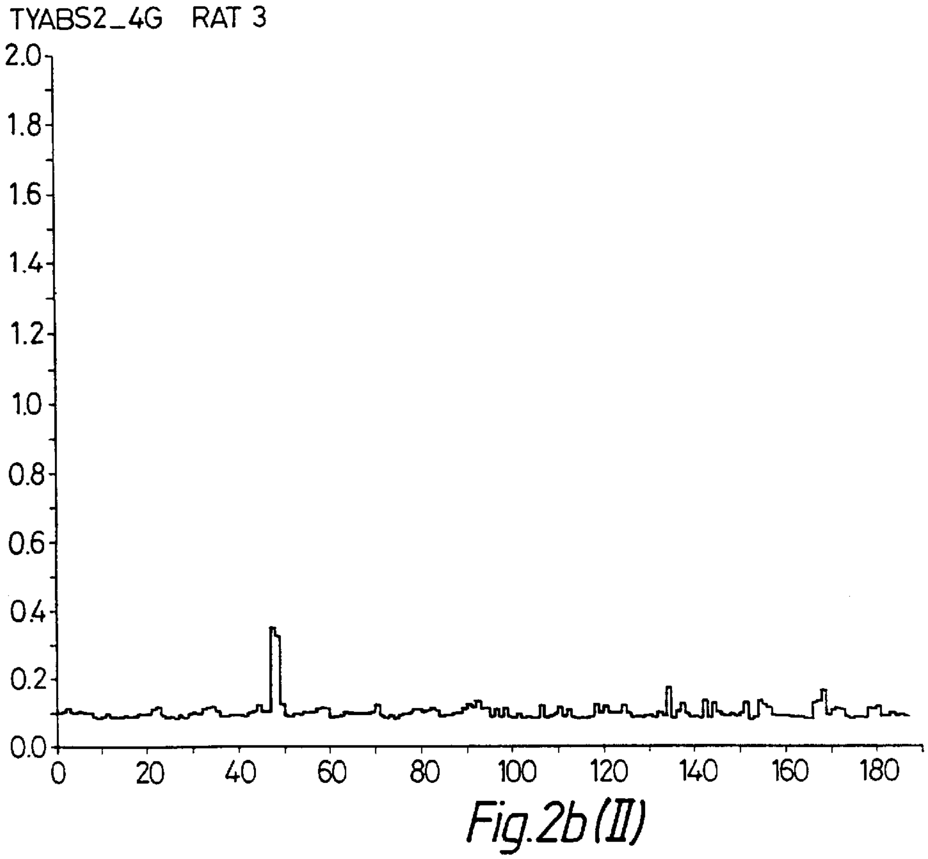
Fig.2b(II)

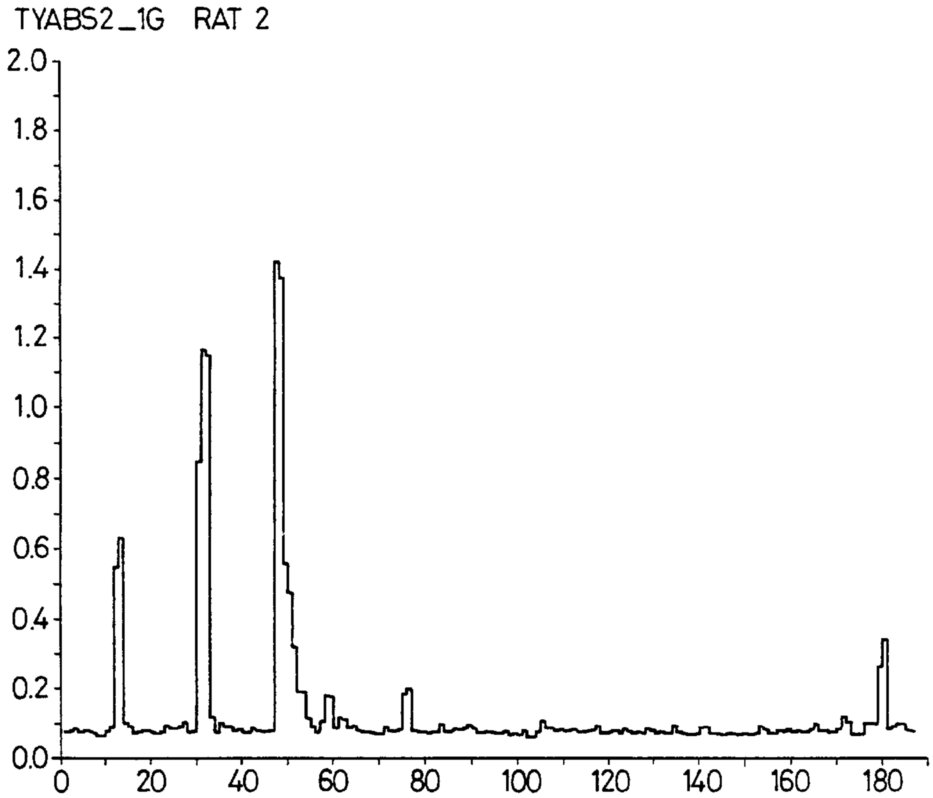
Fig.2c(I)
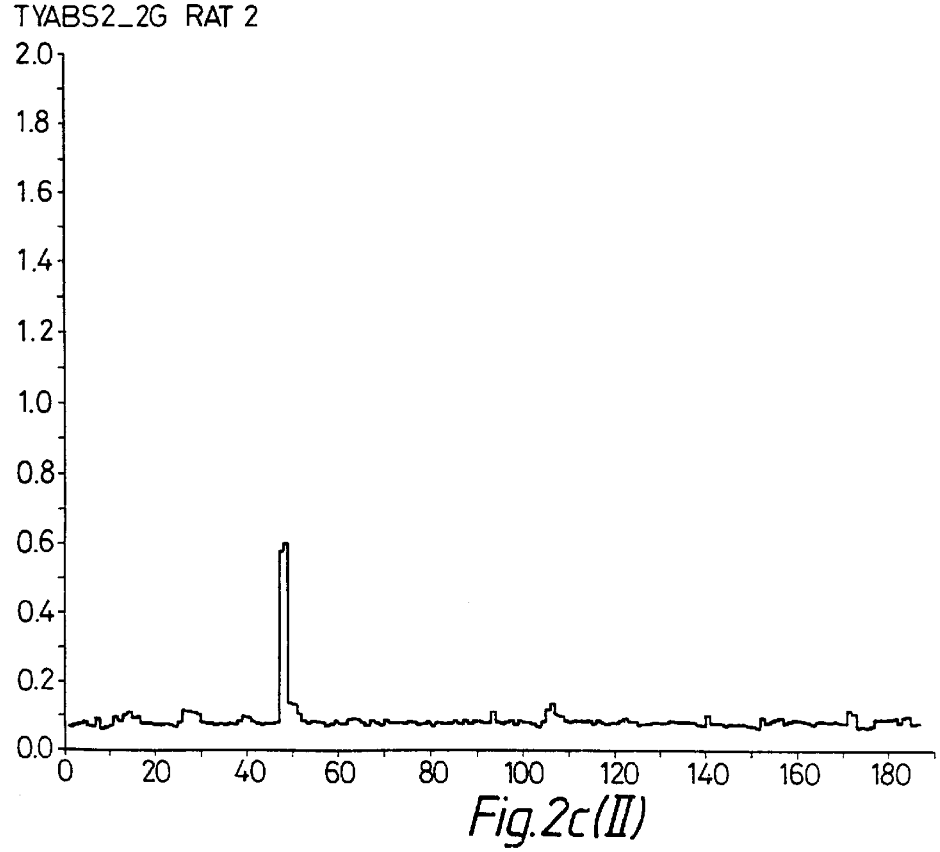
Fig.2c(II)

CHIMERIC VIRUS-LIKE PARTICLE ANTIGEN PRESENTATION AND DELIVERY SYSTEM

The present invention relates to biologically useful particles. In particular it relates to modified particles derived from the yeast retrotransposon Ty. Particles formed from such proteins are immunogenic and can be used in immunotherapeutic or prophylactic vaccines or as diagnostic agents.

An ideal immunogen is a polymer of multiple antigen determinants assembled into a high molecular weight, particulate complex. A substantial disadvantage of most antigens produced by recombinant DNA techniques for vaccines is that they are usually produced as simple monomeric proteins. This is not the ideal configuration of an immunising antigen as it does not readily permit the cross-linking of the components of the immune system. Such crosslinking is required for maximum stimulations of humoral and cellular immunity. For these reasons it would be advantageous to develop polyvalent, particulate carrier systems for immunising antigens.

WO-A-8803562 and WO-A-8803563 describe the use of certain fusion proteins derived from retrotransposons or RNA retroviruses for pharmaceutical, diagnostic or purification applications. Such particles are designated virus-like particles (VLPs) when derived from the yeast retrotransposon Ty. The above published PCT applications note that polyvalent particles are useful for immunisation purposes because their polyvalent nature provides that more antibodies will be raised against the particulate antigens used. The particles are formed of fusion proteins having a particle-forming sequence and, in some embodiments at least, an antigenic sequence. In the examples, the antigenic sequence is positioned C-terminal to the particle-forming sequence.

While the above approach is promising, a potential difficulty is that insertion of the antigen at the C-terminal end of the particle-forming protein may not in all cases be optimal for presentation to the immune system. Animals immunised with recombinant VLPs may elicit a higher titre response to the Ty component than to the added antigen. It would therefore be highly advantageous to construct antigen-presenting particles where the antibody response to the added antigen is augmented. Such particles might also have enhanced ability to stimulate a cell-mediated immune response, such as a T-cell response, a Cytotoxic T-lymphocyte (CTL) reponse or a Natural Killer (NK) cell response. It would further be advantageous if, following immunisation with such particles, the antibody response to the particle-forming moiety was reduced or preferably prevented.

One way to improve the presentation of the antigenic sequence to the immune system might be to insert the antigenic sequence of interest within the particle-forming sequence. However, correct insertion of the antigenic site within the particle-forming protein is likely to be critical for particle formation. Insertions might disrupt the secondary and tertiary structure determinants of the monomer, or the quaternary interactions between monomers necessary for particle formation.

One approach to deduce suitable surface-exposed insertion sequences has been to use the understanding of the three-dimensional structure of viruses elucidated by X-ray crystallography. Such precise analysis of the structure of the polio virus has enabled particulate chimaeric proteins to be created whereby heterologous antigenic sequences are substituted for amino-acids present in the suface-exposed epitopes of this virus (Dedieu et al., J. Virol. (1992) 66 3161–3167; Burke et al, Nature (1988) 332 81–82; Evans et al., Nature (1989) 339 385–388). However, these polio virus constructions are limited by the need to produce a viable virus; even some very short sequences cannot be tolerated.

Detailed analysis as described for poliovirus is not possible for proteins which have not yet been crystallised. Where particles have a well-characterised tertiary β-barrel structure, internal insertions of heterologous antigenic sequences into presumed surface exposed regions have been made using predictive models based on sequence alignment. For example, hybrid particles prepared from the hepatitis B core antigen and an antigen derived from a virus with an analogous secondary structure were found to maintain particle formation and enhance the immunogenicity of the inserted antigen (Schodel et al., J. Virol. (1992) 66 106–114; Brown et al., Vaccine 1991 9 595–601). Substitutions of heterologous peptides into presumed surface-exposed, immunodominant regions of the hepatitis B surface antigen also gave rise to particulate, chimaeric proteins with enhanced immunogenicity (von Brunn et al., Vaccine 1991 9 477–601), although considerable amounts of lipid were found to be associated.

However, retrotransposons have a very poorly understood structure and it is not currently believed that they possess a β-barrel (Bums et al., J. Mol. Biol. (1990) 261 207–211). Suitable sites for insertion of antigens into these particulate proteins are therefore not known or predictable. In retroviruses (which have a very similar structure to retrotransposons) it has been shown that insertion of an antigen into the middle of the gag sequence destroys the particle-forming nature of this sequence (Luo et al., Proc Natl. Acad. Sci. USA 89 10527–10531 (1992)).

The present inventors have identified the surface-exposed immunodominant epitopes within the yeast retrotransposon Ty p1. Immunogenic sites are not necessarily surface exposed; high titre antibodies are frequently elicited against core proteins during viral infections even though such proteins are not exposed on the surface of the particle (eg the influenza nucleoprotein). The inventors have also found that insertion of heterologous antigenic sequences into such epitopes does not prevent particle formation. In retrotransposons the size of insertion which can be tolerated without disrupting particle formation appears to be remarkably large; much greater than has been described for any other system, where generally substitutions have been preferred. The resulting hybrid particles exhibit reduced immunogenicity of the particle forming protein, and an enhanced immune reponse to the inserted sequence.

According to a first aspect of the invention, there is provided a non-natural particle-forming protein comprising a first self-assembling particle forming amino acid sequence substantially homologous with a yeast retrotransposon Ty p1 protein and a second amino acid sequence, wherein the second sequence is antigenic and is incorporated within an epitope of the first amino acid sequence, which epitope, on particles formed from the first amino-acid sequence alone, is surface-exposed.

Such constructions may be produced either by insertion of antigenic sequences into these surface epitopes to form true hybrid proteins, or by substitution of the native amino acids found at such sites with the amino acid sequence of interest, or by a combination of deletion, substitution and insertion.

The surface-expressed epitopes will generally be found in the N-terminal half of the first particle forming protein, the sequence of which is disclosed in Dobson et al., 1984

EMBO J. 3 1115. In particular, three consensus surface-exposed regions have been identified in the N-terminal half of the particle-forming protein p1 of the retrotransposon Ty, located at amino acids 21–42 (position A) amino acids 55–74 (position B) and amino acids 93–142 (position C) as shown in FIG. 1 and summarised in Table 1. Proteins in which the second amino acid sequence is located within at least one of these regions in the first amino acid sequence are preferred. Within these regions, any suitable insertion site may be chosen for the second sequence. These sites include those between amino-acids 30–31, 67–68, 113–114 and 132–133 of the Ty protein and have been designated sites A, B, $C_1$ and $C_2$ respectively, but other sites are equally appropriate.

Particles derived from Ty may have advantages over those derived from polio or Hepatitis for use as vaccines. Pre-exposure to hepatitis or polio vaccines can compromise an effective subsequent reponse against the chimaera. The use of particles derived from Ty is therefore preferable, as there will be less likelihood of a patient having a pre-existing immunological response. Since Ty is not a pathogen, vaccination with Ty will not cause exposure to pathogenic antigens.

The expression "substantially homologous", when describing the relationship of an amino acid sequence to a natural protein, means that the amino acid sequence can be identical to the natural protein or can be an effective but truncated or otherwise modified form of the natural protein or can share at least 50%, 60%, 70%, 80%, 90%, 95% or 99%, in increasing order of preference, of the residues of the natural protein or its modified form. "Effective" means that the particle forming ability of the natural protein is retained (or at least not substantially lost). Alternatively or in addition, a nucleic acid sequence encoding the amino acid sequence may hybridise, for example under stringent conditions, to a nucleic acid sequence encoding the natural protein or its truncated form, or would do so but for the degeneracy of the genetic code. Stringent hybridisation conditions are known and are exemplified by approximately 0.9 molar salt concentration at approximately 35° to 65° C.

The antigenic sequence may correspond to a sequence derived from or associated with an aetiological agent or a tumour. The aetiological agent may be a microorganism such as a virus, bacterium, fungus or parasite. The virus may be: a retrovirus, such as HIV-1, HIV-2, HTLV-I, HTLV-II, HTLV-III, SIV, BIV, LAV, EIAV, CAEV, murine leukaemia virus, Moloney murine leukaemia virus, and feline leukaemia virus; an orthomyxovirus, such as influenza A or B; a paramyxovirus, such as parainfluenza virus, mumps, measles, RSV and Sendai virus; a papovavirus, such as HPV; an arenavirus, such as LCMV of humans or mice; a hepadnavirus, such as Hepatitis B virus; a herpes virus, such as HSV, VZV, CMV, or EBV. The tumour-associated or derived antigen may for example be a proteinaceous human tumour antigen, such as a melanoma-associated antigen, or an epithelial-tumour associated antigen such as from breast or colon carcinoma.

The antigenic sequence may be also derived from a bacterium, such as of the genus Neisseria, Campilobacter, Bordetella, Listeria, Mycobacteria or Leishmania, or a parasite, such as from the genus Plasmodium, especially *P. falciparum,* or from a fungus, such as from the genus Candida, Aspergillus, Cryptococcus, Histoplasma or Blastomyces.

The antigenic sequence may typically vary in length from between 6 and 60 amino acids, for example 6–50, 6–40, or 6–30, although it is not possible with precision to give universally appropriate maxima and minima. The sequence should be sufficiently long to give rise to the desired immunogenic response, but not so long as to cause unacceptable distortion to the rest of the molecule.

Preferred antigenic sequences are antigenic sequences corresponding to epitopes from a retrovirus, a paramyxovirus, an arenavirus or a hepadna virus, or a from human tumour cell. Examples include known epitopes from:

1) HIV (particularly HIV-1) gp120,
2) HIV (particularly HIV-1) p24,
3) Influenza virus nucleoprotein and haemagglutinin,
4) LCMV nucleoprotein,
5) HPV L1, L2, E4, E6 and E7 proteins,
6) p97 melanoma associated antigen,
7) GA 733-2 epithelial tumour-associated antigen,
8) MUC-1 epithelial tumour-associated antigen,
9) Mycobacterium p6,
10) Malaria CSP or RESA antigens,
11) VZV gpI, gpII or gpIII Particularly preferred antigenic sequences comprise a sequence substantially homologous with an antigenic portion of the third variable domain of a lentivirus. This region, known as the V3 loop or GPGR loop is found between amino acids 300 and 330 of the envelope glycoprotein gp120 of HIV-1 and in analogous positions of other lentiviruses. The V3 loop is defined by two flanking cysteine residues linked by a disulphide bond and, for HIV-1 at least, is the major neutralising epitope of the virus (Putney et al 1986 *Science* 234, 1392; Rusche et al 1988 *Proc. Natl. Acad. Sci.* 85, 3198; Palker et al 1988 *Proc. Natl. Acad. Sci.* 85 1932; and Goudsmit et al 1988 *AIDS* 2 157). The antigenic portion of choice may constitute the whole or half of the V3 loop. However, a conserved sequence of the V3 loop may be useful in conferring immunity against more than one isolate of a virus (such as HIV-1).

A number of isolates of HIV-1, in which the sequence of the V3 loop varies from isolate to isolate, are known. The most common isolates are HXBII, RF and MN; MAL, ELI and BH10 are also important, but the MN isolate may be the most clinically relevant. Laboratory isolate IIIB is a mixture of strains BH10 and HXBII. The invention is not limited to sequences derived from the V3 loop of any particular isolate, some of which are shown below.

| | | |
|---|---|---|
| BH10 | SNCTRPNNNTRKSIRIQRGPGRAFVTIGKIGNMRQAHCNISG | (SEQ ID NO: 12) |
| HXBII | SNCTRPNNNTRKRIRIQRGPGRAFVTIGKIGNMRQAHCNISG | (SEQ ID NO: 13) |
| MN | SNCTRPNYNKRKRIHIGPGRAFYTTKNIIGTIRQAHCNISG | (SEQ ID NO: 14) |
| MAL | SNCTRPGNNTRRGIHFGPGQALYTTGIVDIRRAYCTING | (SEQ ID NO: 15) |

-continued

| | | |
|---|---|---|
| RF | SNCTRPNNNTRKSITKGPGRVIYATGQIIGDIRAHCNLSGS | (SEQ ID NO: 16) |
| ELI | STCARPYQNTRQRTPIGLGQSLYTTRSRSIIGQAHCNISG | (SEQ ID NO: 17) |

Neither is the invention limited to natural V3 loop sequences. Examples of variant V3 loop sequences which can be used in the invention include:

| | | |
|---|---|---|
| MAL(var) | SNCTRPGNNTRRGIHFGPGQALYTTGIVDEIRRAYCNISG | (SEQ ID NO: 18) |
| RF(var) | SNCTRPNNNTRKSITKQRGPGRVLYATGQIIGDIRKAHCNSIG | (SEQ ID NO: 19) |
| ELI(var) | STCARPYQNTRQRTPIGLGQSLYTTRGRTKIIGQAHCNISG | (SEQ ID NO: 20) |

A comparison of the sequences of the V3 loop from many different HIV-1 isolates shows great variation between isolates. Antibodies raised against the V3 loop are therefore usually type-specific. However, approximately 60% of isolates to date have the consensus sequence GPGRAF SEQ ID NO: 21, and more than 80% have a GPGR sequence at the tip of the loop. Recent studies have shown that immunisation with peptides containing the GPGRAF SEQ ID NO: 21 consensus sequence or cross-immunisation with recombinant gp120 from different isolates can induce antibodies which cross react between isolates. The GPGRAF SEQ ID NO: 21 consensus sequence may itself be used in the invention.

Other embodiments of the invention involve the use of short sequences of V3 which are not necessarily conserved between various isolates. Whatever V3-derived or V3-related sequence is used, the resulting fusion proteins, or at least particles assembled from them, will be similar antigenically to natural V3 loop sequences in the sense that they cross-react with one or more common antibodies.

More than one V3-derived sequence can be present in a fusion protein of the invention. This embodiment may enable a single fusion protein to be useful in the protection against more than one HIV isolate: therefore, V3-derived sequences from different HIV isolates can be present on the same molecule.

More generally, it will be appreciated that the invention provides considerable flexibility in the nature of the antigenic, second amino acid sequences and the way in which they (if there are more than one) can be located within the first amino acid sequence. For example, two or more identical second amino acid sequences can be inserted in tandem into the same insertion site, two or more identical second amino acid sequences can be inserted into different insertion sites, two or more different second amino acid sequences can be inserted in different insertion sites (or even a single insertion site), and it will be appreciated that the two or more different amino acid sequences may be derived from different epitopes of the same antigen.

As fusion proteins in accordance with the invention spontaneously assemble into particles, it is possible by means of the invention to prepare multivalent particles.

According to a second aspect of the invention, there is provided a particle comprising a plurality of non-natural proteins as described above. Particles in accordance with the invention may contain a heterologous, or, preferably, homologous population of proteins. Each protein may have any of the configurations described above.

According to a third aspect of the invention, there is provided nucleic acid (particularly DNA) coding for a fusion protein as described above. It will generally be the case that the nucleic acid will be capable of being expressed without splicing or anti-termination events. There will generally be no frame shifting, but frame shifting is not necessarily always excluded.

Further according to the present invention is provided a vector including nucleic acid as described above.

Expression vectors in accordance with the invention will usually contain a promoter. The nature of the promoter will depend upon the intended host expression cell. For yeast, PGK is a preferred promoter, but any other suitable promoter may be used if necessary or desirable. Examples include GAPD, GAL1-10, PH05, ADH1, CYC1, Ty delta sequence, PYK and hybrid promoters made from components from more than one promoter (such as those listed). For insect cells, preferred promoters are the polyhedrin and p10 promoters from *Autographica californica* nuclear polyhedrosis virus (AcNPV). Those skilled in the art will be able to determine other appropriate promoters adapted for expression in these or other cells. Vectors not including promoters may be useful as cloning vectors, rather than expression vectors.

The invention also includes host cells, for examples bacterial cells, such as *E. coli,* which may be used for genetic manipulation, yeast cells such as *Saccharomyces cerevisiae* or *Pichia pastoris* or animal cells.

The augmented immunogenic nature of the particles in accordance with the invention, facilitates the production of antibodies with specific characteristics. The invention thus further provides antibodies raised or directed against particulate antigens of the invention; such antibodies may be polyclonal or monoclonal. For the production of human monoclonal antibodies, hybridoma cells may be prepared by fusing spleen cells from an immunised animal with a tumour cell. Appropriately secreting hybridoma cells may thereafter be selected.

Particulate antigens in accordance with the invention may be used in the preparation of vaccines, for example immunotherapeutic vaccines, which form a further aspect of the invention. The vaccine may comprise a particulate antigen and a physiologically acceptable non-toxic carrier, such as sterile physiological saline or sterile PBS. Sterility will generally be essential for parenterally administrable vaccines. One or more appropriate adjuvants may also be present, but are not always necessary. Examples of suitable adjuvants include muramyl dipeptide compounds such as prototype muramyl dipeptide, aluminium hydroxide and saponin.

Vaccines in accordance with the invention may present more than one antigen. Either a cocktail of different particulate antigens may be used, or a homogeneous population of particulate antigens having more than one epitope could be used, as described above. It may in practice be simpler for a vaccine to contain a mixture of different particulate antigens.

Fusion protein and particulate antigens of this invention are useful as diagnostic reagents. Particulate antigens for diagnostic purposes are particularly advantageous because they can be physically separated by centrifugation or filtration and can be directly dispersed on solid supports such as glass or plastic slides, dip sticks, macro or micro beads, test tubes, wells of microtitre plates and the like. The particulate antigens of this invention may also be dispersed in fibrous or bibulous materials such as absorbent disk (U.S. Pat. No. 4,632,901), strips or chromatography columns as the solid support. The particles and fusion proteins readily adhere to solid supports. The particles may after purification be disrupted into fusion proteins and the fusion proteins may be dispersed on surfaces as indicated above. These reagents are useful for a variety of diagnostic tests. For example, a test sample suspected of having antibody to the particulate antigen and fluorescent, enzyme or radio-labelled antibody is competitively reacted with the particulate antigen or fusion protein on a solid support and the amount of labelled antibody which binds to the particulate antigen on the solid support. Particulate antigens of this invention are also useful for agglutination reactions with antibodies. Those skilled in the diagnostic arts will recognise a wide variety of application of particulate antigens and fusion proteins of this invention for diagnostic purposes.

Preferred features for each aspect of the invention are as for the first aspect mutatis mutandis.

The following examples illustrate the invention, but are not intended to limit the scope in any way. The examples refer to the accompanying drawings, in which;

FIG. 1 shows Pepscan analysis of mouse sera. Each plot shows $OD_{492}$ (abscissa) versus peptide number (ordinate) from 1 at the N-terminus to 187 at the truncated C terminus of p1, showing the reactivity of each peptide to antibodies in the test serum. Each test serum is from the pooled sera of five inbred mice immunised with OGS200 VLPs ( described below) in the indicated adjuvant.

| | | |
|---|---|---|
| Figure 1a: RIBI; | 1b: SAF-1; | 1c: Chemivax |
| 1d: normal mouse serum | 1e: Alum | 1f: unadjuvanted |

FIG. 2 shows data from pre-absorption experiments used to determine epitope surface accessability in three separate rats. The upper plots show Pepscan activities in sera from rats immunised with OGS200 VLPs in alum. The lower plots show the same sera after preincubation with MA5260 VLPs at 4° C. overnight and Pepscan analysis. The loss of reactivity with the peptides is due to sequestration of antibodies by epitopes at the surface of the native VLP. The loss of reactivity is specific for certain epitopes.

FIG. 3 shows a summary of surface accessibility of epitopes of p1. The sera used for this summary are from two rabbits immunised with MA5260 VLPs in Freunds and three rats immunised with OGS200 VLPs in alum. The discontinuous bar represents those areas of the p1 protein recognised in the pepscan analysis by antibodies in these sera.

EXAMPLE 1

Identification of Epitopes in D1

Figure 1A:
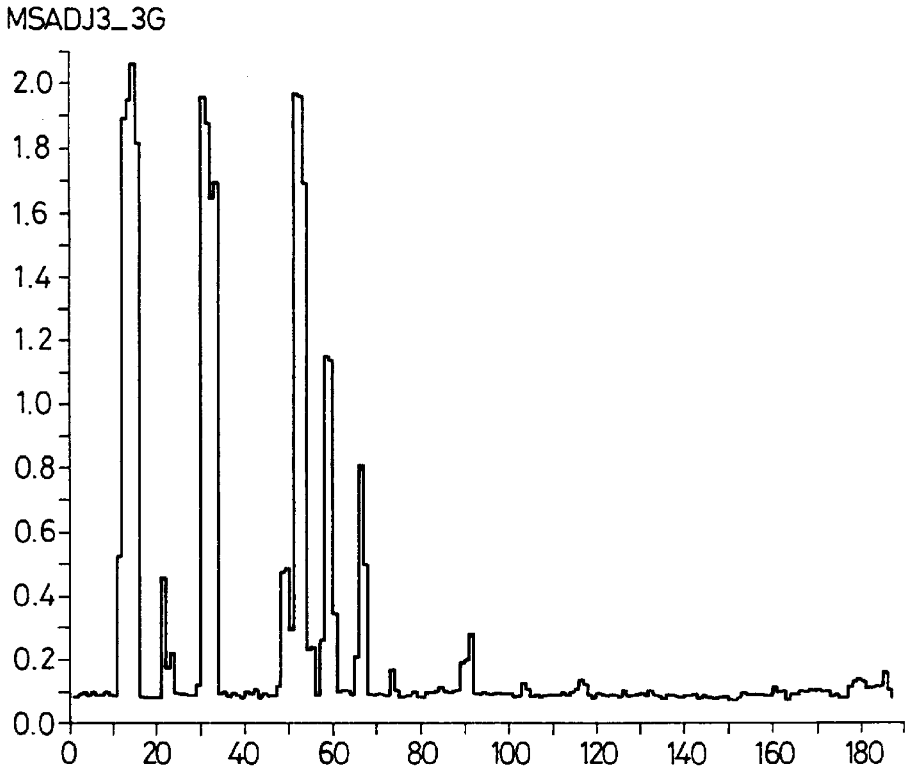
Figure 1B:
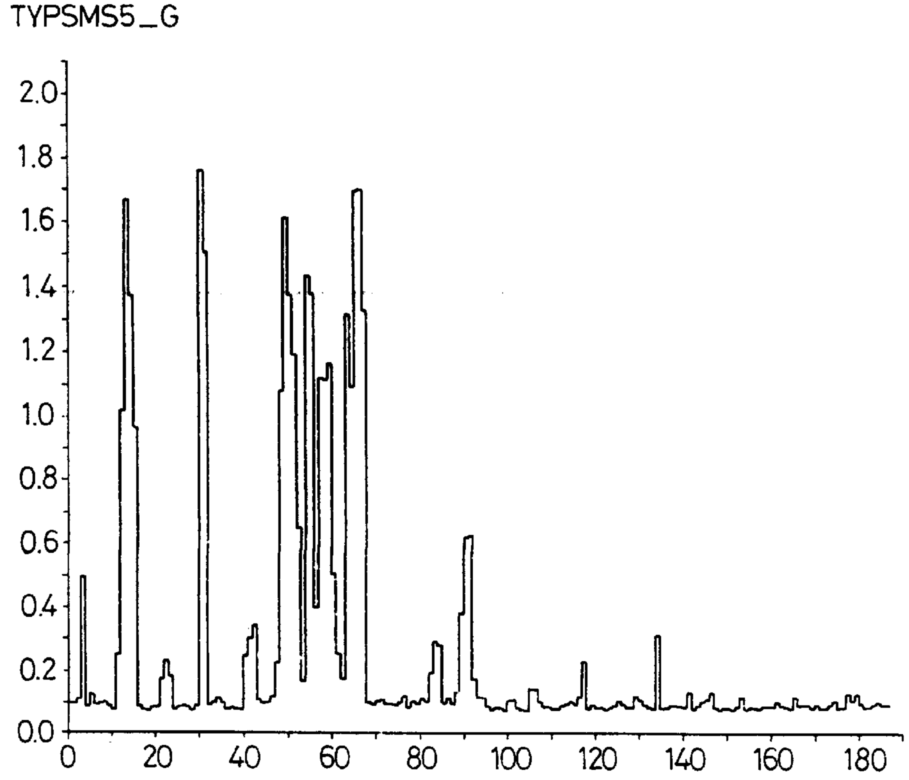
Figure 1C:
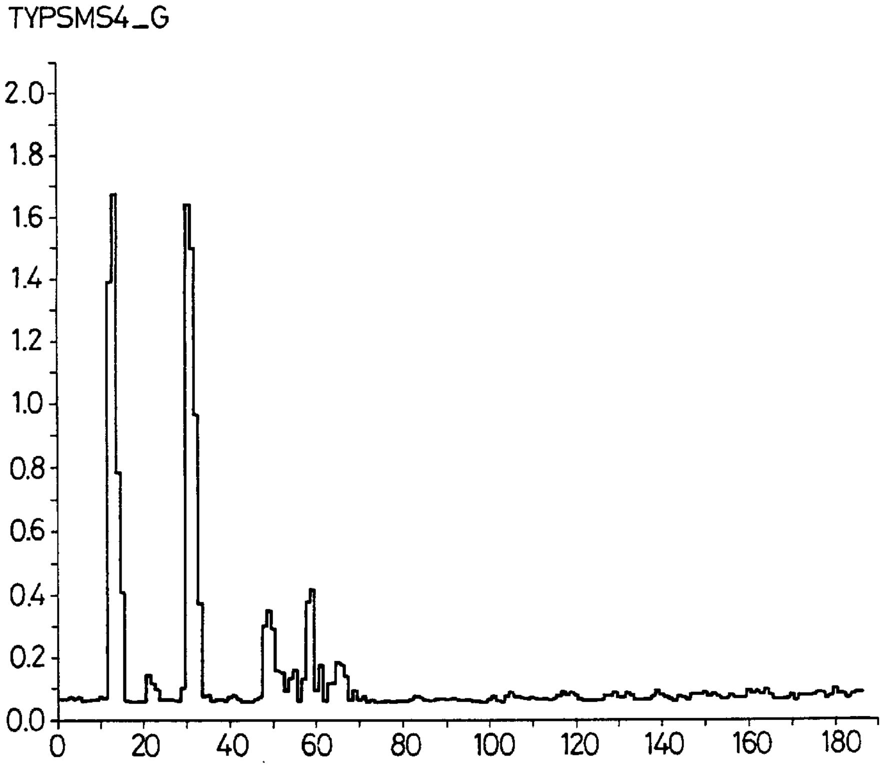
Figure 1D:
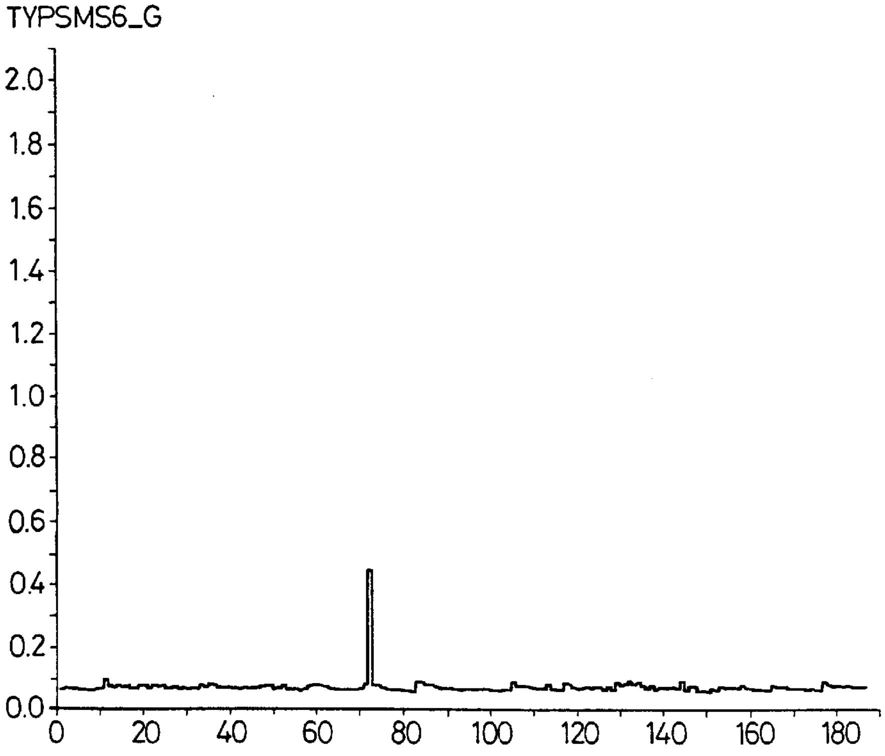
Figure 1E:
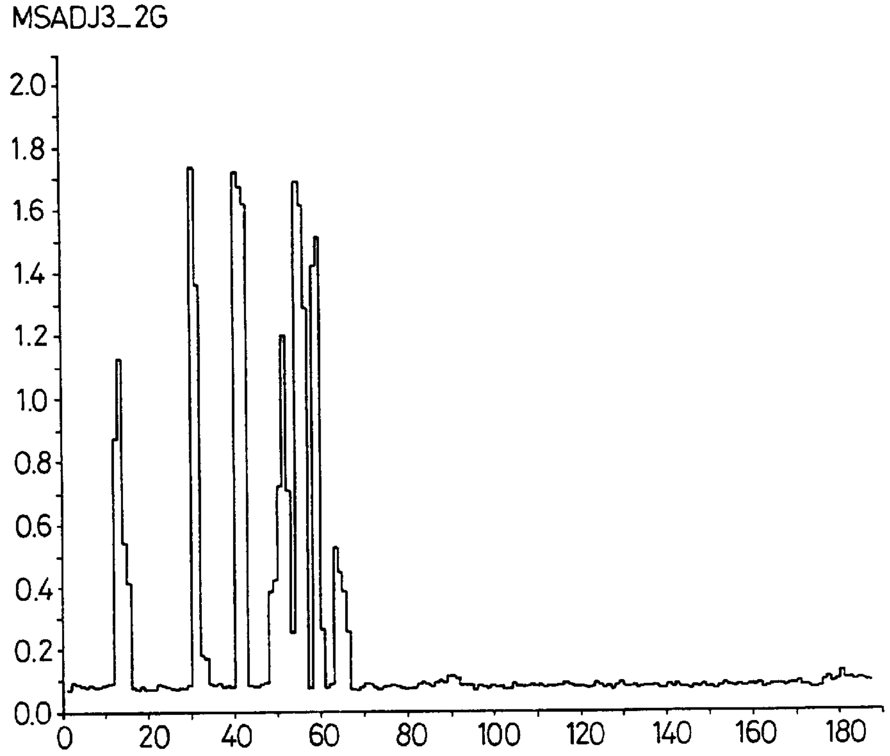
Figure 1F:
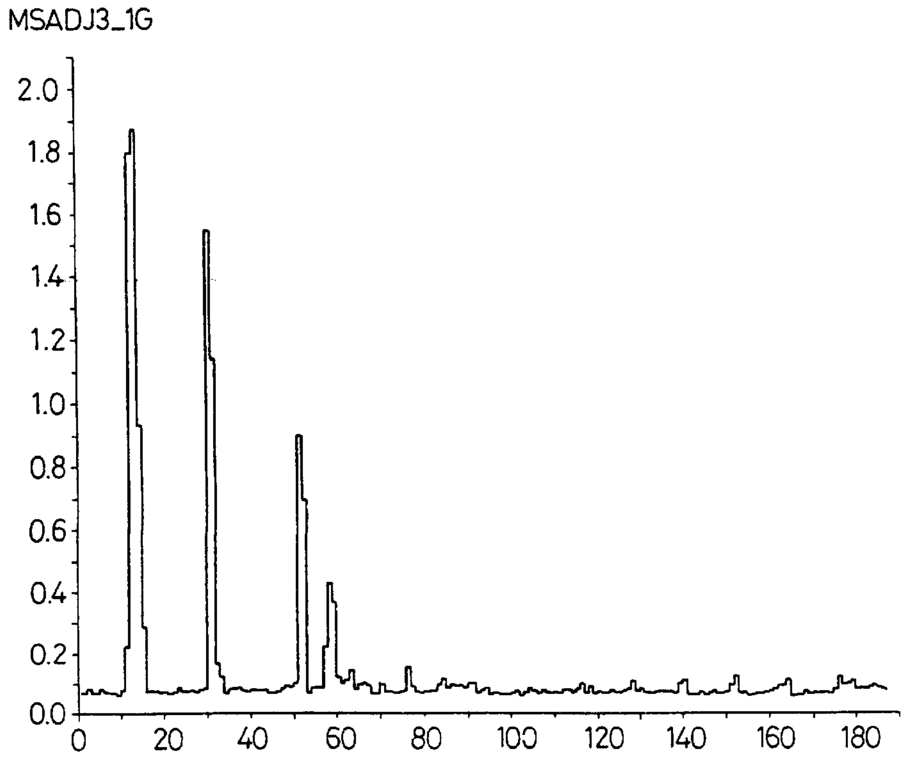

The PEPSCAN™ kit (CRB, Cambridge) which was prepared for Ty comprises 10-mer peptides overlapping by 8 residues corresponding to the entire length of the wild type p1 protein of Ty 1. 187 peptides cover the truncated p1 protein. Each well of a microtitre plate was coated with a peptide and the anti-Ty test serum overlaid. Antibody binding to epitope peptides was detected by a secondary antibody conjugate and a colorimetric reaction.

Sera from five species (human, macaque, rabbit, rat and mouse) were obtained following immunisation with a variety of VLPs (OGS200: p1 -HIVp24 (disclosed in WO-A-8803562), MA5620: p1 alone (disclosed in WO-A-8803563), OGS561: p1-IIIB:MN:RF V3 loops and OGS530.

OGS 561 is a derivative of pOGS 40, which is disclosed in copending patent application PCT/GB92/01545. At the 3'end of TyA gene are three consecutive V3 loops, in order HXBII, MN, RF. These comprise the amino acid sequences SNCTRPNNNTRKRIRIQRG-PGRAFVTIGKIGMMRQAHCNISG (SEQ ID NO: 1) SNCTRPNYNKRKRIHIGPGRAFYTTKNI-IGTIRQAHCNISG (SEQ ID NO: 2) SNCTRPNNNTRK-SITKGPGRVIYATGQIIGDIRKAHCNLSGS (SEQ ID NO: 3) which are linked by Bam H1 sites which encode two redundant amino acids glycine and serine. The corresponding nucleotide sequences could readily be determined by persons skilled in the art.

pOGS 530 (and pOGS 531 discussed below) are derivatives of pOGS 40, which is disclosed in copending patent application PCT/GB92/01545. These have an oligonucleotide insertion in the Bam H1 site which encodes the MN (Example 10) or HXBII V3 loop respectively. The immunisarions were carried ou in different adjuvants (alum, RIBI DETOX™, CHEMIVAX™, SAF-1 or Freund's complete). Sera were analysed by PEPSCAN™. FIG. 1 shows a typical raw data set from pooled groups of five mice immunised with OGS200 VLPs in different adjuvants. A summary of peptides recognised by all the sera tested is collated in Table 1. The number of epitopes is, to some extent, adjuvant dependent. A summary of the mouse data from FIG. 1 is shown in Table 2 to illustrate this dependence by comparing no adjuvant, alum, CHEMIVAX, RIBI and SAF-1. The use of any of the four adjuvants elicits antibodies to more epitopes than no adjuvant. SAF-1 causes antibodies to be raised to more epitopes (8) than RIBI (5), CHEMIVAX (4) and alum (4). A similar effect has been seen in rabbits. Sera from rabbits immunised with OGS200 VLPs in alum recognised a total of 8 p1 epitopes, whereas with SAF-1 12 epitopes were recognised (Table 1). Freund's appears to be the most powerful adjuvant. Nineteen p1 epitopes were recognised by sera from rabbits immunised with OGS5620 VLPs in Freund's (Table 1)

The choice of epitopes for engineering is extensive; however three "consensus" epitopes emerge from the data. These are contained within peptides 11–17, 28–33 and a larger region covered by peptides 47–68. These correspond to amino acid residues 21–42, 55–74 and 93–142 of the p1 protein and have been named A, B and C, respectively. They are recognised by the overwhelming majority of sera, irrespective of the immunising VLP and the adjuvanting regime.

Table 1 shows the reactivity of animal sera to p1 peptides in the Pepscan analysis. Each cell in the table shows the number of responders over background, blanks indicate no response. Of the 16 human clinical trial sera tested, only one had a sufficiently high anti-Ty titre to give reliable reactivities in the Pepscan analysis. Eliminating the remaining 15 non-responders, the maximum possible score in the total column is 33. The three 'consensus' epitopes, A, B and C correspond to the peptides 11–17, 28–33 and 47–68, respectively.

Table 2 shows the serum reactivities of mice immunised with OGS200 VLPs in a variety of adjuvants. All immunisations were intramuscular. The shaded rows correspond to the three "consensus" epitopes, A, B and C at peptides 11–17, 28–33 and 47–68.

two rabbits immunised with MA5620 VLPs in Freund's were incubated with native purified MA5620 VLPs. These sera were then analysed by PEPSCAN™. Antibodies to surface accessible epitopes bind to the surface of the native VLP and are therefore unavailable to bind to the PEPSCAN™ peptides. Where an epitope is surface accessible, a loss of previously observed reactivity with that epitope indicates that it is a surface feature. The preabsorption experiments were controlled for proteolysis of the native VLP by serum proteases by analysing the particles post-absorption by western blot.

TABLE 1

| Peptide Number | Human OGS200 Alum | Macaque OGS200 Alum | Rat OGS200 Alum | Rat OGS561 Alum | Mouse OGS200 Various | Rabbit OGS200 Alum | Rabbit OGS200 SAF-1 | Rabbit MA5620 Freunds | Rat MA5620 Alum | Total |
|---|---|---|---|---|---|---|---|---|---|---|
| 1–6 | | 4/4 | | 2/5 | 1/5 | 4/5 | 4/5 | 2/2 | | 17 |
| 11–17 | 1/16 | 4/4 | 5/5 | 5/5 | 5/5 | | 5/5 | 2/2 | 1/1 | 28 |
| 21–23 | | | | | 3/5 | 1/5 | | | | 4 |
| 24–27 | | 3/4 | | 2/5 | | 2/5 | 1/5 | 2/2 | | 10 |
| 28–33 | 1/16 | 3/4 | 5/5 | 5/5 | 5/5 | 4/5 | 5/5 | 2/2 | 1/1 | 31 |
| 37–42 | 1/16 | 3/4 | | | 2/5 | | | 1/2 | | 7 |
| 47–68 | 1/16 | 4/4 | 5/5 | 5/5 | 5/5 | 5/5 | 5/5 | 2/2 | 1/1 | 33 |
| 72–77 | | 2/4 | | 2/5 | | 3/5 | 4/5 | 1/2 | | 12 |
| 81–85 | 1/16 | 3/4 | 1/5 | 2/5 | 1/5 | | 1/5 | 1/2 | | 10 |
| 88–92 | 1/16 | | | 3/5 | 2/5 | | | 1/2 | | 7 |
| 101–102 | | 1/4 | | | | | | 2/2 | | 3 |
| 112–118 | | 4/4 | | 1/5 | | | 4/5 | 2/2 | | 11 |
| 128–134 | | 4/4 | 3/5 | | | | 4/5 | 2/2 | 1/1 | 14 |
| 139–140 | 1/16 | 4/4 | 1/5 | 1/5 | | | | 2/2 | | 9 |
| 144–146 | | | 2/5 | 4/5 | | | 1/5 | | | 7 |
| 150–151 | | | 3/5 | | | | | 2/2 | | 5 |
| 157–161 | | 1/4 | | 1/5 | | | 1/5 | 1/2 | 1/1 | 5 |
| 169–171 | | 1/4 | 1/5 | | | | | 2/2 | | 4 |
| 175–182 | | 3/4 | 5/5 | 2/5 | | 1/5 | 4/5 | 2/2 | 1/1 | 18 |
| 185–187 | | | | | | 1/5 | | 1/2 | | 2 |

TABLE 2

| Peptide | ADJUVANT | | | | |
|---|---|---|---|---|---|
| Number | None | Alum | Ribi | Chemivax | SAF-1 |
| 1–6 | – | – | – | – | + |
| 11–17 | + | + | + | + | + |
| 21–23 | – | – | + | + | + |
| 28–33 | + | + | + | + | + |
| 37–42 | – | + | – | – | + |
| 47–68 | + | + | + | + | + |
| 81–85 | – | – | – | – | + |
| 88–92 | – | – | + | – | + |

Figure 3:
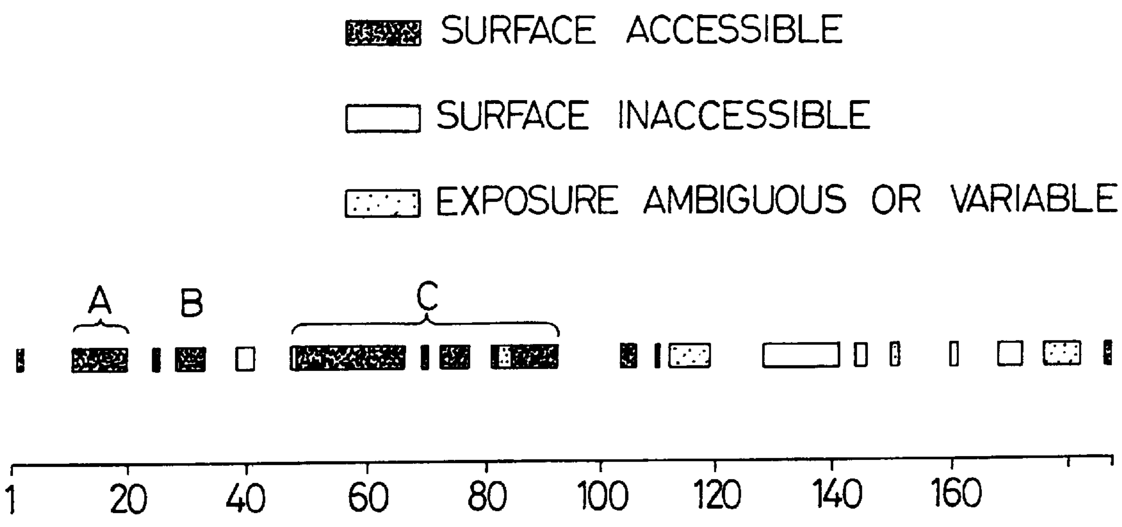

FIG. 2 shows the PEPSCAN™ data from three rat sera before and after preabsorption. These data show that epitopes in the N terminal half of p1 are mostly surface accessible whereas those in the C terminal half of the protein are mainly inaccessible. The three major linear epitopes, A, B and C identified above, all showed surface accessibility. A diagrammatic summary of preabsorption experiment data is shown in FIG. 3 which illustrates the accessibility of linear epitopes of p1. The gaps are due to regions of the protein not recognised by antibodies in any of the sera tested. This analysis demonstrates that surface accessibility, where information is available, is essentially limited to the N terminal half of p1.

EXAMPLE 2

Identification of Surface Epitopes of p1

PEPSCAN™ analysis will identify any well defined linear epitope of p1. Since the analysis is based on recognition of short linear peptides, conformational or non-contiguous epitopic determinants are unlikely to be detected. In addition, PEPSCAN™ data do not distinguish between surface (ie accessible to the antibody) or buried epitopes of the native VLP.

Serum preabsorption studies were used to determine which regions of p1, and in particular which of the three epitopes identified above, are surface accessible. Sera from three rats immunised with OGS200 VLPs in alum and from

EXAMPLE 3

Choice of p1 Epitopes for Engineering

The three consensus epitopes identified satisfy several criteria for selection as targets for insertion of antigen: they are recognised by sera from all species tested irrespective of the VLP type used as an immunogen and the adjuvanting regime; and all are surface exposed.

Figure 4:
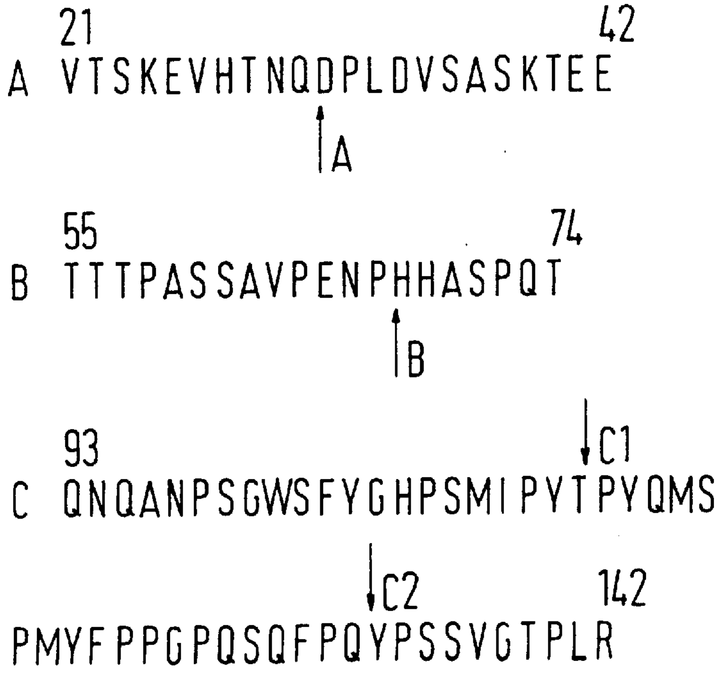
FIG. 4 shows the location of the insertion sites A, B, C1 and C2 within the regions A, B and C of p1, as defined by the reactive peptides in the Pepscan analysis. The numbers at the end of each sequence are the p1 amino acid coordinates.

Four insertion points within the p1 protein were chosen, one each in A and B, and two in C. These lie between amino acids 30–31, 67–68, 113–114 and 132–133 and are referred to as A, B, C1 and C2 respectively (see FIG. 4). Although these four sites were chosen for evaluation, other positions within the defined regions A, B and C may be equally appropriate as insertion sites.

EXAMPLE 4

Manipulation of the TYA(d) Gene

The TyA (d) gene was manipulated to introduce a unique Nhe I restriction site at insetion points A, B, C1 or C2 to allow insertion of foreign DNA sequences. Four versions were thus constructed, one for each of the four insertion points selected. The vectors containing this modification were prepared as follows. A BglII/BamH1 restriction fragment containing the coding sequence of the TyA(d) gene was excised from pOGS 226 and inserted into the vector pSP46 also digested with BglII/BamH1, to give pOGS460 (pSP46 is a derivative of pSP64 in which the HindIII site in the polylinker has been converted to a BglII site). pOGS 460 was then digested with NheI (restriction site present within pSP46) and PstI (restriction site present within TyA gene) to release a 1117bp fragment. This was then inserted into M13 mp18 digested with XbaI and PstI. Using site directed mutagenesis, an Nhe I restriction site was then introduced at the insertion points A, B, C1 or C2 (ie between TyA nucleotides 90–91, 201–202, 339–340 and 396–397 respectively)

The NheI site was used for insertion of double stranded (ds) oligonucleotides encoding each of three size variants of the MN isolate V3 loop.

The mutagenised TyA(d) sequences were removed from M13 as BglII/SplI fragments and ligated into the vector backbone of BglII/SplI digested pOGS440. The SplI restriction site in the TyA (d) gene is 5' to the Pst I site.

| These manipulations yielded the following plasmid constructions: | |
|---|---|
| pOGS810 is the pOGS440 equivalent with the NheI site at position | A |
| pOGS811 is the pOGS440 equivalent with the NheI site at position | B |
| pOGS812 is the pOGS440 equivalent with the NheI site at position | $C_1$ |
| pOGS813 is the pOGS440 equivalent with the NheI site at position | $C_2$ |

pOGS440 was constructed as follows. pKV560 is described by Chambers et al., (1989) Mol. Cell. Bio. 9 5516–5524. pKV572 is identical to pKV560 with the exception that the interferon sequences are removed leaving a BglII cloning site. pKV572 contains the minimal assay promoter with a 5' BamH1 cloning site for upstream activating sequences, and is the starting point for pJC87. A 1 kb EcoR1-Xho 1 fragment from pUG4IS containing the GAL-10 promoter sequence was purified. This was further digested with Dde1 and a 510 base pair fragment isolated. The 5' protruding ends of this fragment were filled-in with the Klenow fragment of DNA polymerase and BglII oligonucleotide linkers added.

Figure 5:
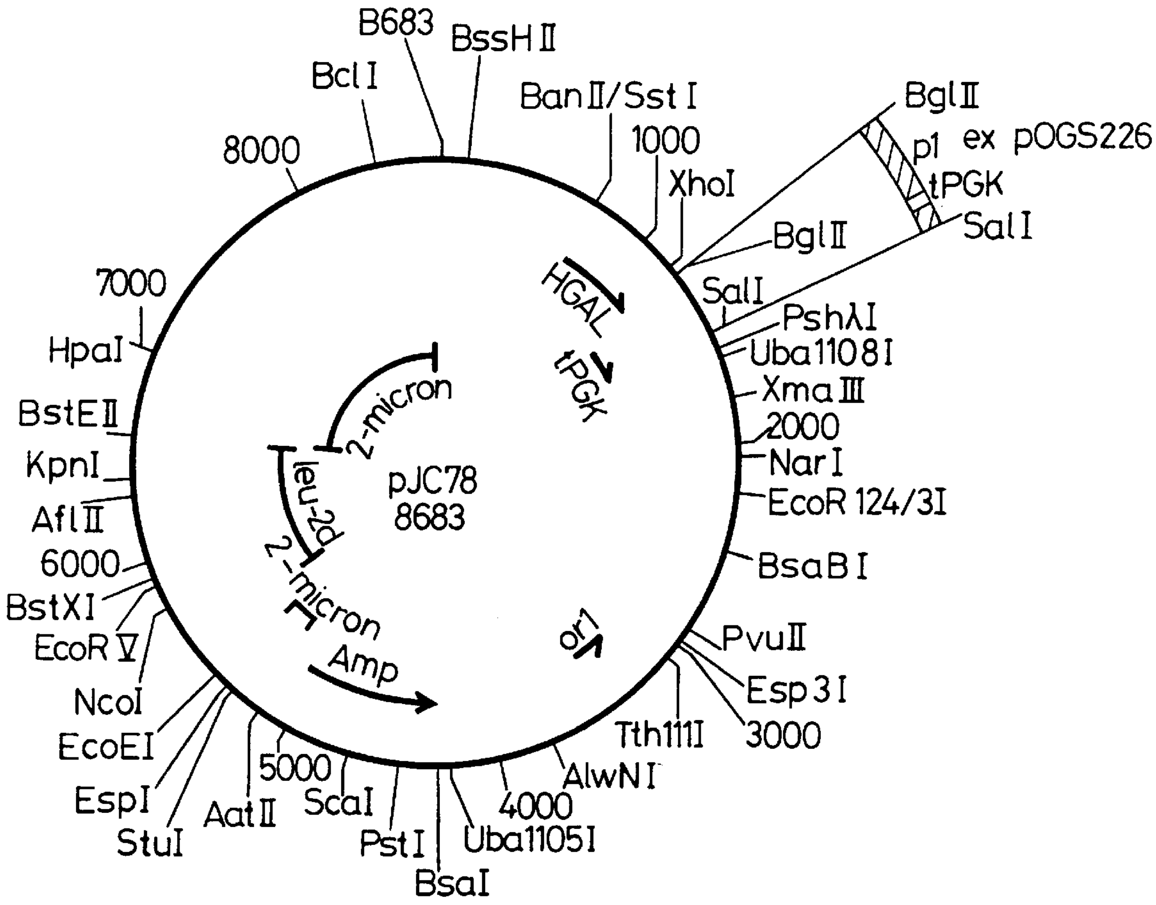
FIG. 5 shows plasmid pOGS440.

The fragment was then digested with Sau3A and a 360 base pair fragment purified. This fragment was ligated into BamH1 digested, phosphate treated pKV572. The ligated products were transformed into HW87 and the resultant plasmids screened for the orientation of the insert by DNA sequencing. A clone which had the 360 base pair GAL1–10 Dde1-Sau3A fragment in the GAL1 orientation was selected and called pJC78.

pOGS440 is shown in FIG. 5; it was constructed by inserting the BglII/SalI fragment from pOGS226 (a derivative of pMA5620 described in WO-A-8803563 which has an additional BglII site inserted adjacent to the N-terminus of p1) into BglII/SalI at pJC78.

EXAMPLE 5

Particle Formation by Insertion Site Mutants of p1

Insertion of an NheI restriction site into the TyA(d) gene as described in Example 4 resulted in the introduction of two additional amino acids (Alanine and Serine) into the p1 protein. It was necessary to confirm that this change did not interfere with particle formation for any of the chosen insertion sites (A, B, C1 or C2).

Plasmids pOGS810, pOGS811, pOGS812 and pOGS813 were transformed into *S. cerevisiae* strain MC2, although any available strain could be used. The transformed cells were cultured, harvested and the VLPs isolated by fractionation on sucrose gradients as follows.

Yeast cells were grown selectively at 3° C. to a density of $8\times10^6$ cells/ml. The cells were then collected by low speed centrifugation, washed once in ice-cold water and resuspended in TEN buffer (10 mM Tris, pH 7.4, 2mM EDTA, 140 mM NaCl) at 1 ml per 1 liter of cells. The cells were disrupted by vortexing with glass beads (40-mesh, BDH), at 4° C. until >70% were broken. The beads were pelleted by low speed centrifugation (2,000 g), then the supernatant was collected, and the debris removed by centrifugation at 13,000 g for 20 minutes.

The clarified supernatant was transferrred to a SW28 tube and underlayered with 3ml of 60% w/v sucrose solution in TEN. Tubes were then centrifuged at 28K rpm for 90 minutes to band the VLPs at the sucrose interface.

VLPs were recovered and dialysed against TEN to remove the sucrose, then purified further by banding on a pre-formed linear (10–60%) sucrose gradient (SW41 tubes centrifuged at 25 krpm for 6 hours). The VLPs were recovered, dialysed and concentrated.

All four constructions expressed particulate p1 protein at levels comparable to the positive control for the experiment, pOGS440, demonstrating that addition of the two residues at the insertion points does not adversely affect particle formation.

EXAMPLE 6

Insertion of Antigen (GPGRAF)$^3$

Complementary pairs of DNA oligonucleotides were synthesised encoding the central six residues (GPGRAF) (SEQ ID NO: 21) of the gp120 V3 loop from the MN isolate. These are $(5'CTAGTGGTCCAGGTAGAGCTTTCT3')_3$ (SEQ ID NO: 4)

The ends of the annealed double stranded oligonucleotide are compatible with NheI cut ends for ligation into the unique NheI sites within pOGS810–813. Transformants were initially screened for the absence of the NheI site which is abolished by oligonucleotide insertion before DNA sequencing for verification. Three tandemly repeated copies were inserted at position B in the TYA(d) gene of pOGS811, to generate pOGS814. The coding consequence of this is as follows:

P E N P A S G P G R A F S S G P G R A F S S G P G R A F S S H H A S P. (SEQ ID No: 5)

The residues in bold are the inserted amino acids flanked by the wild type p1 residues. The A S and S S motifs are encoded by the NheI cohesive ends of the oligonucleotide. Construction of the $(GPGRAF)_3$ insert has provided information on the size of insert that can be tolerated at position B. Since this 26 residue insertion allows particle formation, insertion of the 20 and 40 residue V3 loop size variants should be tolerated at that position. It also supports the notion that the original Ty epitope is in the form of a surface loop which can be extended without interfering with the normal fold of the p1 monomer.

EXAMPLE 7

Insertion of Antigen: GPGRAF SEQ ID NO: 21

Oligonucleotides encoding for GPGRAF SEQ ID NO: 21 with NheI compatible ends were synthesised as described above.

Once annealed they were ligated into each of the four insertion sites. Once the oligonucleotide was inserted, the NheI site was abolished. Resulting transformants were therefore screened for loss of the NheI site. The orientation of the insert was verified by DNA sequencing. The resulting constructions are numbered as follows:

| | | |
|---|---|---|
| pOGS815: | pOGS810 with GPGRAF at postion A | SEQ ID NO: 21 |
| pOGS816: | pOGS811 | B |
| pOGS817: | pOGS812 | C1 |
| pOGS818: | pOGS813 | C2 |

The total inserted sequence is as follows:

A S G P G R A F S S (SEQ ID NO: 6)

The AS and SS residues flanking the N and C termini of the inserted antigen respectively are encoded by the altered NheI sites at each end of the inserted oligonucleotide.

*S. cerevisiae* strain MC2 yeast cells were transformed with each plasmid.

EXAMPLE 8

Insertion of Antigen: Half V3 loop

Complementary pairs of DNA oligonucleotides

```
5'CTAGTAAAAGAAAGAGAATTCATATTGGTCCAGGTAGAGCTTTCTATAC (SEQ ID NO: 7)
TACCAAAAACATTATCG3'
```

were synthesised that encode the following sequence:

A S K R K R I H I G P G R A F Y T T K N I I A S (SEQ ID NO: 8)

The flanking AS residues are those encoded by the NheI compatible oligonucleotide ends. The annealed oligonucleotide possessed an EcoRI restriction site. Once ligated into the vector the 5' NheI site was abolished while the 3' NheI site was recreated. The remaining 3' NheI site enables further antigens to be added if desired. Transformants were screened by EcoRI restriction digestion and the orientation of insertion was determined by DNA sequencing. The resulting constructions are numbered as follows:

| | | |
|---|---|---|
| pOGS819: | pOGS810 with the half V3 loop at position | A |
| pOGS820: | pOGS811 | B |
| pOGS821: | pOGS812 | C1 |
| pOGS822: | pOGS813 | C2 |

EXAMPLE 9

Insertion of Antigen: Whole V3 loop

Two pairs of complementary pairs of DNA oligonucleotides

| |
|---|
| 5'CTAGTATTAATTGCACCCGTCCTAACTACAATAAAAGAAAGAGAATTCA (SEQ ID NO: 9) TATTGGTCCAGGT3' and |

| |
|---|
| 5'AGAGCTTTCTATACTACCAAAAACATTATCGGTACTATTAGACAAGCTC (SEQ ID NO: 10) ACTGTAATATCG3' |

were synthesised that together encode the whole V3 loop sequence as follows:

A S I N $C^S$ T R P N Y N K R K R I H I G P G R A F Y T T K N I I G T I R Q A H $C^S$ N I A S. (SEQ ID NO: 11)

The flanking AS residues were encoded by the NheI compatible ends and $C^S$ signifies the cysteine residues thought to close the loop at its base by a disulphide bond. The whole insert was constructed in two parts which were ligated together before ligation into the appropriate vectors. As with the half loop oligonucleotides, the 5' NheI site is abolished on insertion and the 3' NheI site is recreated. The inserted sequence also carries an EcoRI restriction site to aid screening. The resulting transformants were screened for the presence and orientation of the DNA fragment by restriction enzyme digestion. The three ligation junctions, at each end and in the middle of the insert, were verified by DNA sequencing. The constructions were numbered as follows:

| | | |
|---|---|---|
| pOGS823: | pOGS810 with whole V3 loop at position | A |
| pOGS824: | pOGS811 | B |
| pOGS825: | pOGS812 | C1 |
| pOGS826: | pOGS813 | C2 |

EXAMPLE 10

Characterisation of pOGS814 VLPs: $(GPGRAF)_3$ at position B

Purified pOGS814 DNA was transformed into *S. cerevisiae* strain MC2, although any available strain could be used. Cells were harvested, hand bead-beaten and the cell homogenate clarified by centrifugation at 9K for 20 minutes. 1.5 ml of this material was then applied to sucrose gradients (15 to 45% with a 60% cushion) and centrifuged at 40 Krpm for 1.5 hours. The gradients were fractionated and examined by SDS-PAGE. The OGS814 protein sedimented with the characteristics of a VLP in a well defined zone half way down the gradient, well resolved from monomeric protein solutes.

EXAMPLE 11

Immunoreactivity of OGS814 VLPs

Fractions from the gradients described in Example 10 were analysed by western blotting with three antibodies: an anti-Ty polyclonal, DuPont gp120 MAb 9305 which reacts with the V3 loop tip sequence—RIQRGPGRAFVTIGK—SEQ ID NO: 22, and Dupont gp120 monoclonal 9284, which reacts with the left-hand side of the V3 loop—NNNTRKSIRIQR—SEQ ID NO: 23. As expected, the OGS814 VLPs reacted with the Ty polyclonal and 9305 MAb, but not with 9284 MAb. The controls were MA5620 VLPs and OGS531 VLPs (whole V3 loop from isolate HXB2 at the C terminus). All the controls had the predicted reactivities. The western blot data are summarised in Table 3.

TABLE 3

Western blot immunoreactivity data from MA5620, OGS814, and OGS531 VLPs with anti-Ty, 9305 and 9284 antibodies

| VLP | Added Antigen | Antigen position | Antibody | | |
|---|---|---|---|---|---|
| | | | anti-Ty | 9305 | 9284 |
| MA5620 | – | – | + | – | – |
| OGS814 | $(GPGRAF)_3$ | B | + | + | – |
| OGS531 | V3 loop | C terminus | + | + | + |

Table 3. Western blot immunoreactivity data from MA5620, OGS814, and OGS531 VLPs with anti-Ty, 9305 and 9284 antibodies.

EXAMPLE 12

Surface Exposure of the Antigen in OGS814 VLPs

The p1 epitope at position B was shown to be surface-exposed in native whole VLPs by its ability to bind its cognate antibody which could then be removed from solution by cosedimentation with the VLP during centrifugation. A similar approach was used to demonstrate that the GPGRAF SEQ ID NO: 21 component of OGS814 at position B is also surface exposed. In this case the cognate antibody was the MAb 9305, shown to recognise OGS814 VLPs. The experiment involved incubation of the VLPs with the MAb, pelleting the VLPs by centrifugation and measuring the amount of unbound MAb left in the supernatant using a V3 peptide ELISA.

In an ELISA for detecting MAbs binding to the 40 amino acid HXB2 gp120 V3 loop peptide, VLPs at 100 and 500 μg/ml or peptide at 200 μg/ml were incubated with 9305 or 9284 MAb at a dilution of 1/100 from the stock. Controls for binding in solution were MA5620 VLPs (negative) and the V3 peptide (positive). The mixtures were centrifuged at 75 Krpm for 15 minutes and the supernatants assayed for residual MAb by ELISA. In summary:

1) the MAbs alone were not removed from solution by centrifugation
2) the negative control MA5620 VLPs bound no antibody, which remained in the supernatant
3) the positive control peptide removed all antibody reactivity from the supernatant, ie no unbound antibody remained
4) OGS814 VLPs bound 9305, but not 9284 antibodies, indicating that the GPGRAF SEQ ID NO: 21 motif in these VLPs is surface accessible

EXAMPLE 13

Immunogenicity of OGS814 VLPs

Rats were imnmunised with purified OGS814 VLPs. Rats were primed at week 0, boosted at weeks 6 and 12, and final bleeds were taken at week 14. Intermediate test bleeds were taken at weeks 6, 8 and 12. Two doses of 50 and 250 μg per immunisation, in the presence and absence of adjuvant are given to four groups of five rats as follows:

| | |
|---|---|
| Group 1 | 50 μg − adjuvant/animal |
| Group 2 | 50 μg + adjuvant/animal |
| Group 3 | 250 μg − adjuvant/animal |
| Group 4 | 250 μg + adjuvant/animal |

EXAMPLE 14

Immunogenicity of OGS822 VLPs

OGS822 VLPs were chosen to examine the improved immunogenicity resulting from the insertion of the half V3 loop within the Ty p1 protein. Rats were immunised intramuscularly with 250 μg purified OGS822 VLPs in aluminium hydroxide adjuvant. Rats were primed at week 0, boosted at weeks 6 and 12, and final bleeds were taken at week 14. Sera were tested for anti-V3 antibody responses both by ELISA and neutralisation assays, the results of which are shown in Table 4.

TABLE 4

| | 4 weeks post-prime | | 2 weeks post boost | |
|---|---|---|---|---|
| ANIMAL | ELISA U/ml | neutralising | ELISA U/ml | neutralising |
| 1 | 21.4 | 320–640 | 28.4 | 1280 |
| 2 | 23.1 | 640 | 44.4 | 1280–2560 |
| 3 | 13.1 | 256 | 11.7 | 320–640 |
| 4 | 8.0 | 256 | 8.2 | 640 |
| 5 | — | 16 | 4.2 | 256 |

Serum antibody and neutralising antibody titres of rats immunised with OGS 822 VLPs. The ELISA data (shown as units/ml) are arbitrary values based on a standard curve produced with a rat anti-MN peptide antiserum. Neutralising antibody titres are expressed as the dilution of serum that resulted in 90% inhibition of syncytia formation in a standard assay.

In the same assays, a pool of antisera from rats immunised with OGS259 VLPs (½ V3 loop at the C-terminus) generated an ELISA value of 2.27 U/ml and a neutralisation titre of 1:8. Insertion of antigen at an internal site (in this case C2) thus resulted in a dramatic improvement in immunogenicity.

EXAMPLE 15

Insertion of Antigen: Influenza nucleoprotein CTL epitope

Complementary pairs of DNA oligonucleotides were synthesised that encode the following sequence:

ASRS TYQRTRALV GSAS (SEQ ID NO: 12)

This contains an influenza nucleoprotein CTL epitope (shown in bold). The flanking ASRS and GSAS amino acids are encoded by restriction enzyme sites. This sequence was inserted into the p1 protein at each of the four sites A, B, $C_1$ and $C_2$.

What is claimed is:

1. A recombinant, chimeric, particle-forming protein comprising a first amino acid sequence consisting of a self-assembling, particle-forming, yeast retrotransposon Ty p1 amino acid sequence and a second antigenic, amino acid sequence which is incorporated within an immunogenic, surface-exposed region of said yeast retrotransposon Ty p1 amino acid sequence, wherein said surface-exposed regions are selected from the group consisting of amino acids 21–42, 55–74, and 93–142 of the Ty p1 sequence.

2. A particle-forming protein as claimed in claim 1 wherein said second amino acid sequence is incorporated into more than one surface-exposed region.

3. A particle-forming protein as claimed in claim 1 wherein the surface-exposed region is present in the N-terminal half of the first amino acid sequence.

4. The particle-forming protein of claim 1, wherein the surface-exposed epitope is located between amino acids 21–42.

5. The particle-forming protein of claim 1, wherein the surface-exposed epitope is located between amino acids 55–74.

6. The particle-forming protein of claim 1, wherein the surface-exposed epitope is located between amino acids 93–142.

7. The particle-forming protein of claim 4 wherein the second amino acid sequence is inserted between amino acids 30–31.

8. The particle-forming protein of claim 5 wherein the second amino acid sequence is inserted between amino acids 67–68.

9. The particle-forming protein of claim 7 wherein the second amino acid sequence is inserted between amino acids 113–114.

10. The particle-forming protein of claim 7 wherein the second amino acid sequence is inserted between amino acids 132–133.

11. The particle-forming protein of claim 1 wherein the second antigenic, amino acid sequence is obtained from a tumor antigen or aetiological agent.

12. The particle-forming protein of claim 11 wherein the second antigenic, amino acid sequence is obtained from an aetiological agent antigen selected from the group consisting of viral, bacterial, fungal, and parasitic antigens.

13. The particle-forming protein of claim 12 wherein the second antigenic, amino acid sequence is obtained from a viral antigen selected from the group consisting of retroviral, orthomyxoviral, paramyxoviral, papovaviral, arenaviral, hepadnaviral and herpes viral antigens.

14. The particle-forming protein of claim 1 wherein the antigenic sequence is between 6 and 60 amino acids inclusive in length.

15. The particle-forming protein of claim 11 wherein the second antigenic amino acid sequence is an epitope selected from the group of antigens consisting of:

1) the Human immunodeficiency virus type 1 gp120, 2) the Human immunodeficiency virus type 1 p24, 3) the Influenza virus nucleoprotein and haemagglutinin, 4) the Lymphocytic choriomeningitis virus nucleoprotein, 5) the Human papilloma virus L1, L2, E4, E6 and E7 proteins, 6) the p97 melanoma associated antigen, 7) the GA 733-2 epithelial tumour-associated antigen, 8) the MUC-1 epithelial tumour-associated antigen, 9) the Mycobacterium antigen p6, 10) the Malarial antigens CSP or RESA, and 11) the Varicella zoster virus antigens gpI, gpII or gpIII.

16. The particle-forming protein of claim 15 wherein the epitope consists of a human immunodeficiency virus type 1 envelope glycoprotein V3 loop.

17. The particle-forming protein of claim 1 wherein two or more of the surface exposed regions have an antigenic amino acid sequence incorporated therein.

18. The particle-forming protein of claim 17 wherein the antigenic amino acid sequence incorporated within one of the surface-exposed regions is different from the antigenic amino acid sequence incorporated within another of the surface-exposed regions.

19. The particle-forming protein of claim 1 wherein more than one antigenic amino acid sequence is incorporated within any single surface exposed region.

20. The particle-forming protein of claim 19 wherein the antigenic amino acid sequences incorporated in any single surface exposed region are not all identical.

21. The particle-forming protein of claim 19 wherein the antigenic amino acid sequences are incorporated in tandem within the surface exposed region.

22. The particle-forming protein of claim 18 wherein the different antigenic amino acid sequences are obtained from different regions of the same antigen.

23. A particle comprising a plurality of homologous proteins as claimed in claim 1.

24. A particle comprising a plurality of heterologous proteins as claimed in claim 1.

25. The particle forming protein of claim 13 wherein the second antigenic amino acid sequence is obtained from a viral antigen selected from the group consisting of human immunodeficiency virus type 1 (HIV-1) antigens, human immunodeficiency virus type 2 (HIV-2) antigens, human T-cell leukemia virus type I (HTLV-I) antigens, human T-cell leukemia virus type II antigens, simian immunodeficiency virus antigens (SIV), bovine immunodeficiency virus (BIV) antigens, EIAV antigens, CAEV antigens, murine leukemia virus antigens, Moloney murine leukemia virus antigens, feline leukemia virus antigens, influenza A virus antigens, influenza B virus antigens, parainfluenza virus antigens, mumps antigens, measles antigens, Rous sarcoma virus antigens, sendai virus antigens, herpes simplex virus antigens, lymphocytic choriomeningitis virus antigens, hepatitis B virus antigens, varicella zoster virus antigens, cytomegalovirus antigens, and Epstein-Barr virus antigens.

* * * * *

UNITED STATES PATENT AND TRADEMARK OFFICE

CERTIFICATE OF CORRECTION

PATENT NO. : 6,060,064
DATED : May 9, 2000
INVENTOR(S) : Sally Elizabeth Adams, et al.

It is certified that error appears in the above-identified patent and that said Letters Patent is hereby corrected as shown below:

Claim 9, column 28,
Line 55, "claim 7" has been deleted and in its place -- claim 6 -- has been inserted.

Claim 10, column 28,
Line 58, "claim 7" has been deleted and in its place -- claim 6 -- has been inserted.

Signed and Sealed this

Ninth Day of October, 2001

*Attest:*

NICHOLAS P. GODICI

*Attesting Officer*

*Acting Director of the United States Patent and Trademark Office*

SEQUENCE LISTING

```
<160> NUMBER OF SEQ ID NOS: 23

<210> SEQ ID NO 1
<211> LENGTH: 42
<212> TYPE: PRT
<213> ORGANISM: Human immunodeficiency virus type 1

<400> SEQUENCE: 1
```

-continued

```
Ser Asn Cys Thr Arg Pro Asn Asn Asn Thr Arg Lys Arg Ile Arg Ile
  1               5                  10                  15

Gln Arg Gly Pro Gly Arg Ala Phe Val Thr Ile Gly Lys Ile Gly Met
             20                  25                  30

Met Arg Gln Ala His Cys Asn Ile Ser Gly
         35                  40


<210> SEQ ID NO 2
<211> LENGTH: 41
<212> TYPE: PRT
<213> ORGANISM: Human immunodeficiency virus type 1

<400> SEQUENCE: 2

Ser Asn Cys Thr Arg Pro Asn Tyr Asn Lys Arg Lys Arg Ile His Ile
  1               5                  10                  15

Gly Pro Gly Arg Ala Phe Tyr Thr Thr Lys Asn Ile Ile Gly Thr Ile
             20                  25                  30

Arg Gln Ala His Cys Asn Ile Ser Gly
         35                  40


<210> SEQ ID NO 3
<211> LENGTH: 42
<212> TYPE: PRT
<213> ORGANISM: Human immunodeficiency virus type 1

<400> SEQUENCE: 3

Ser Asn Cys Thr Arg Pro Asn Asn Asn Thr Arg Lys Ser Ile Thr Lys
  1               5                  10                  15

Gly Pro Gly Arg Val Ile Tyr Ala Thr Gly Gln Ile Ile Gly Asp Ile
             20                  25                  30

Arg Lys Ala His Cys Asn Leu Ser Gly Ser
         35                  40


<210> SEQ ID NO 4
<211> LENGTH: 72
<212> TYPE: DNA
<213> ORGANISM: Artificial Sequence
<220> FEATURE:
<223> OTHER INFORMATION: Description of Artificial Sequence: Three
      tandem repeats of HIV-1 nucleotide sequence further
      comprising restriction enzyme sites.

<400> SEQUENCE: 4

ctagtggtcc aggtagagct ttctctagtg gtccaggtag agctttctct agtggtccag     60

gtagagcttt ct                                                         72


<210> SEQ ID NO 5
<211> LENGTH: 35
<212> TYPE: PRT
<213> ORGANISM: Artificial Sequence
<220> FEATURE:
<223> OTHER INFORMATION: Description of Artificial Sequence: Three
      tandem repeats of a  HIV-1 sequence  further comprising
      residues encoded by restriction enzyme sites.

<400> SEQUENCE: 5

Pro Glu Asn Pro Ala Ser Gly Pro Gly Arg Ala Phe Ser Ser Gly Pro
  1               5                  10                  15

Gly Arg Ala Phe Ser Ser Gly Pro Gly Arg Ala Phe Ser Ser His His
             20                  25                  30

Ala Ser Pro
         35
```

-continued

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: HIV-1 sequence further comprising residues encoded by restriction enzyme sites.

<400> SEQUENCE: 6

```
Ala Ser Gly Pro Gly Arg Ala Phe Ser Ser
  1               5                  10
```

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence: Partial V3 loop of HIV-1 comprising restriction enzyme sites.

<400> SEQUENCE: 7

```
ctagtaaaag aaagagaatt catattggtc caggtagagc tttctatact accaaaaaca     60

ttatcg                                                                66
```

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence: Partial V3 loop of HIV-1 further comprising residues encoded by restriction enzyme sites.

<400> SEQUENCE: 8

```
Ala Ser Lys Arg Lys Arg Ile His Ile Gly Pro Gly Arg Ala Phe Tyr
  1               5                  10                  15

Thr Thr Lys Asn Ile Ile Ala Ser
             20
```

<210> SEQ ID NO 9
<211> LENGTH: 62
<212> TYPE: DNA
<213> ORGANISM: Artificial Sequence
<220> FEATURE:
<223> OTHER INFORMATION: Description of Artificial Sequence: Partial V3 loop of HIV-1 further comprising restriction enzyme sites.

<400> SEQUENCE: 9

```
ctagtattaa ttgcacccgt cctaactaca ataaaagaaa gagaattcat attggtccag     60

gt                                                                    62
```

<210> SEQ ID NO 10
<211> LENGTH: 61
<212> TYPE: DNA
<213> ORGANISM: Artificial Sequence
<220> FEATURE:
<223> OTHER INFORMATION: Description of Artificial Sequence: Partial V3 loop of HIV-1 further comprising restriction enzyme sites.

<400> SEQUENCE: 10

```
agagctttct atactaccaa aaacattatc ggtactatta gacaagctca ctgtaatatc     60
```

-continued g 61

<210> SEQ ID NO 11
<211> LENGTH: 43
<212> TYPE: PRT
<213> ORGANISM: Artificial Sequence
<220> FEATURE:
<223> OTHER INFORMATION: Description of Artificial Sequence: V3 loop of HIV-1 further comprising residues encoded by restriction enzyme sites.

<400> SEQUENCE: 11

```
Ala Ser Ile Asn Cys Thr Arg Pro Asn Tyr Asn Lys Arg Lys Arg Ile
  1               5                  10                  15

His Ile Gly Pro Gly Arg Ala Phe Tyr Thr Thr Lys Asn Ile Ile Gly
             20                  25                  30

Thr Ile Arg Gln Ala His Cys Asn Ile Ala Ser
         35                  40
```

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Influenza nucleoprotein CTL epitope comprising flanking residues encoded by restriction enzyme sites.

<400> SEQUENCE: 12

```
Ala Ser Arg Ser Thr Tyr Gln Arg Thr Arg Ala Leu Val Gly Ser Ala
  1               5                  10                  15

Ser
```

<210> SEQ ID NO 13
<211> LENGTH: 42
<212> TYPE: PRT
<213> ORGANISM: Human immunodeficiency virus type 1

<400> SEQUENCE: 13

```
Ser Asn Cys Thr Arg Pro Asn Asn Asn Thr Arg Lys Ser Ile Arg Ile
  1               5                  10                  15

Gln Arg Gly Pro Gly Arg Ala Phe Val Thr Ile Gly Lys Ile Gly Asn
             20                  25                  30

Met Arg Gln Ala His Cys Asn Ile Ser Gly
         35                  40
```

<210> SEQ ID NO 14
<211> LENGTH: 42
<212> TYPE: PRT
<213> ORGANISM: Human immunodeficiency virus type 1

<400> SEQUENCE: 14

```
Ser Asn Cys Thr Arg Pro Asn Asn Asn Thr Arg Lys Arg Ile Arg Ile
  1               5                  10                  15

Gln Arg Gly Pro Gly Arg Ala Phe Val Thr Ile Gly Lys Ile Gly Asn
             20                  25                  30

Met Arg Gln Ala His Cys Asn Ile Ser Gly
         35                  40
```

<210> SEQ ID NO 15
<211> LENGTH: 39
<212> TYPE: PRT

-continued

<213> ORGANISM: Human immunodeficiency virus type 1

<400> SEQUENCE: 15

```
Ser Asn Cys Thr Arg Pro Gly Asn Asn Thr Arg Arg Gly Ile His Phe
  1               5                  10                  15

Gly Pro Gly Gln Ala Leu Tyr Thr Thr Gly Ile Val Asp Ile Arg Arg
             20                  25                  30

Ala Tyr Cys Thr Ile Asn Gly
         35
```

<210> SEQ ID NO 16
<211> LENGTH: 41
<212> TYPE: PRT
<213> ORGANISM: Human immunodeficiency virus type 1

<400> SEQUENCE: 16

```
Ser Asn Cys Thr Arg Pro Asn Asn Asn Thr Arg Lys Ser Ile Thr Lys
  1               5                  10                  15

Gly Pro Gly Arg Val Ile Tyr Ala Thr Gly Gln Ile Ile Gly Asp Ile
             20                  25                  30

Arg Ala His Cys Asn Leu Ser Gly Ser
         35                  40
```

<210> SEQ ID NO 17
<211> LENGTH: 40
<212> TYPE: PRT
<213> ORGANISM: Human immunodeficiency virus type 1

<400> SEQUENCE: 17

```
Ser Thr Cys Ala Arg Pro Tyr Gln Asn Thr Arg Gln Arg Thr Pro Ile
  1               5                  10                  15

Gly Leu Gly Gln Ser Leu Tyr Thr Thr Arg Ser Arg Ser Ile Ile Gly
             20                  25                  30

Gln Ala His Cys Asn Ile Ser Gly
         35                  40
```

<210> SEQ ID NO 18
<211> LENGTH: 40
<212> TYPE: PRT
<213> ORGANISM: Human immunodeficiency virus type 1

<400> SEQUENCE: 18

```
Ser Asn Cys Thr Arg Pro Gly Asn Asn Thr Arg Arg Gly Ile His Phe
  1               5                  10                  15

Gly Pro Gly Gln Ala Leu Tyr Thr Thr Gly Ile Val Asp Glu Ile Arg
             20                  25                  30

Arg Ala Tyr Cys Asn Ile Ser Gly
         35                  40
```

<210> SEQ ID NO 19
<211> LENGTH: 43
<212> TYPE: PRT
<213> ORGANISM: Human immunodeficiency virus type 1

<400> SEQUENCE: 19

```
Ser Asn Cys Thr Arg Pro Asn Asn Asn Thr Arg Lys Ser Ile Thr Lys
  1               5                  10                  15

Gln Arg Gly Pro Gly Arg Val Leu Tyr Ala Thr Gly Gln Ile Ile Gly
             20                  25                  30

Asp Ile Arg Lys Ala His Cys Asn Ser Ile Gly
```

-continued

```
        35                  40


<210> SEQ ID NO 20
<211> LENGTH: 41
<212> TYPE: PRT
<213> ORGANISM: Human immunodeficiency virus type 1

<400> SEQUENCE: 20

Ser Thr Cys Ala Arg Pro Tyr Gln Asn Thr Arg Gln Arg Thr Pro Ile
  1               5                  10                  15

Gly Leu Gly Gln Ser Leu Tyr Thr Thr Arg Gly Arg Thr Lys Ile Ile
             20                  25                  30

Gly Gln Ala His Cys Asn Ile Ser Gly
         35                  40


<210> SEQ ID NO 21
<211> LENGTH: 6
<212> TYPE: PRT
<213> ORGANISM: Human immunodeficiency virus type 1

<400> SEQUENCE: 21

Gly Pro Gly Arg Ala Phe
  1               5


<210> SEQ ID NO 22
<211> LENGTH: 15
<212> TYPE: PRT
<213> ORGANISM: Human immunodeficiency virus type 1

<400> SEQUENCE: 22

Arg Ile Gln Arg Gly Pro Gly Arg Ala Phe Val Thr Ile Gly Lys
  1               5                  10                  15


<210> SEQ ID NO 23
<211> LENGTH: 12
<212> TYPE: PRT
<213> ORGANISM: Human immunodeficiency virus type 1

<400> SEQUENCE: 23

Asn Asn Asn Thr Arg Lys Ser Ile Arg Ile Gln Arg
  1               5                  10
```